United States Patent [19]

Drewes et al.

[11] Patent Number: 5,185,026
[45] Date of Patent: Feb. 9, 1993

[54] HERBICIDAL NAPHTHALENE DERIVATIVES

[75] Inventors: Mark W. Drewes, Langenfeld; Michael Haug; Klaus Lürssen, both of Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 680,495

[22] Filed: Apr. 4, 1991

[30] Foreign Application Priority Data

Apr. 11, 1990 [DE] Fed. Rep. of Germany ....... 4011696
Oct. 24, 1990 [DE] Fed. Rep. of Germany ....... 4033808

[51] Int. Cl.$^5$ ............... A01N 43/54; C07D 239/60; C07D 405/06; C07D 239/28
[52] U.S. Cl. .................. 504/225; 544/296; 544/300; 544/301; 544/302; 504/196; 504/239; 504/243; 504/197; 504/242; 504/165; 504/168
[58] Field of Search ............. 544/296, 300, 301, 302; 71/92

[56] References Cited

U.S. PATENT DOCUMENTS

| | | | |
|---|---|---|---|
| 4,871,387 | 10/1989 | Sasse et al. | 71/92 |
| 4,979,982 | 12/1990 | Brouwer et al. | 71/92 |
| 4,986,846 | 1/1991 | Gohbara et al. | 71/92 |

FOREIGN PATENT DOCUMENTS 360163 3/1990 European Pat. Off.

*Primary Examiner*—Mukund J. Shah
*Assistant Examiner*—Matthew V. Grumbling
*Attorney, Agent, or Firm*—Sprung Horn Kramer & Woods

[57] ABSTRACT

Herbicidal naphthalene derivatives of the formula in which

Q represents oxygen, sulphur or the group NR, where R represents hydrogen or alkyl,
$R^1$ represents hydrogen or alkyl
$R^2$, $R^3$ and $R^4$ are identical or different and in each case represent hydrogen or another radical,
$R^5$ represents hydrogen or halogen, or represents in each case optionally substituted alkyl, alkoxy, alkylthio, alkylamino or dialkylamino,
$R^6$ represents hydrogen or halogen, or represents in each case optionally substituted alkyl or alkoxy, and
$R^7$ represents hydrogen or halogen, or represents in each case optionally substituted alkyl, alkoxy, alkylthio, alkylamino or dialkylamino, and
Z represents N—$R^8$ or $$\diagup\!\!\!\!\!\!{}^{R^9}_{C}\diagdown\!\!\!\!\!\!{}_{R^{10}}$$

9 Claims, No Drawings

HERBICIDAL NAPHTHALENE DERIVATIVES

The invention relates to new naphthalene derivatives, to processes for their separation, and to their use as herbicides.

It has already been disclosed that certain naphthalene derivatives such as, for example, 2-(4,6-dimethoxypyrimidin-2-yl-oxy)-1-naphthaldehyde, have herbicidal properties (cf. EP-A 360,163; JP-A 2,056,469).

However, the herbicidal activity of the naphthalene derivatives which have been disclosed and their compatibility with crop plants is not always entirely satisfactory.

The new naphthalene derivatives of the general formula (I) have now been found,

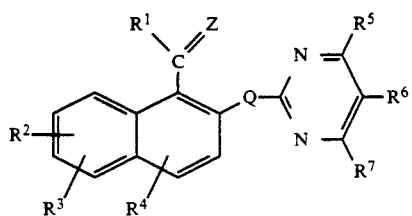

in which
Q represents oxygen, sulphur or the group NR where R represents hydrogen or alkyl,
$R^1$ represents hydrogen or alkyl,
$R^2$, $R^3$ and $R^4$ are identical or different and in each case represent hydrogen, hydroxyl, amino, cyano, nitrogen or halogen, or represent in each case optionally substituted alkyl, alkoxy, alkylthio, alkylsulphinyl or alkylsulphonyl,
$R^5$ represents hydrogen or halogen, or represents in each case optionally substituted alkyl, alkoxy, alkylthio, alkylamino or dialkylamino,
$R^6$ represents hydrogen or halogen, or represents in each case optionally substituted alkyl or alkoxy and
$R^7$ represents hydrogen or halogen, or represents in each case optionally substituted alkyl, alkoxy, alkylthio, alkylamino or dialkylamino, and
Z represents one of the following groups: N—$R^8$ or

where
$R^8$ represents hydrogen, hydroxyl, amino or carbamoylamino, or represents in each case optionally substituted alkyl, alkenyl, alkynyl, alkoxy, alkenyloxy, alkoxycarbonylalkoxy, alkylamino, dialkylamino, alkylcarbonylamino, alkoxycarbonylamino, alkylsulphonylamino, aryl, aralkyl, aryloxy, aralkyloxy, arylamino, diarylamino, aralkylamino, N-alkyl-N-arylamino, hetarylamino, hetarylcarbonylamino, arylcarbonylamino or arylsulphonylamino,
$R^9$ represents hydrogen, halogen, cyano, carboxyl, alkoxycarbonyl, alkylcarbonylamimo or dialkoxyphosphoryl, and
$R^{10}$ represents formyl, cyano, carboxyl, hydroxymethyl or carbamoyl, or represents in each case optionally substituted alkoxycarbonyl, cycloalkoxycarbonyl, alkylthiocarbonyl, alkylaminocarbonyl, cycloalkylaminocarbonyl, dialkylaminocarbonyl, alkylaminocarbonylalkoxycarbonyl, dialkylaminocarbonylalkoxycarbonyl, arylaminocarbonylalkoxycarbonyl, N-alkyl-N-arylaminocarbonylalkoxycarbonyl, pyrrolidinylcarbonyl, piperidinylcarbonyl, morpholinylcarbonyl, piperazinylcarbonyl, aryloxycarbonyl, aralkyloxycarbonyl, heterocyclylalkoxycarbonyl, arylthiocarbonyl, aralkylthiocarbonyl, arylaminocarbonyl, aralkylaminocarbonyl, N-alkyl-N-arylaminocarbonyl, arylhydrazinocarbonyl, alkylhydrazinocarbonyl or phthalimidoxycarbonyl, or $R^{10}$ together with $R^9$ represents the group —CO—O—$(CH_2)_n$—, where n represents the numbers 1 to 4.

The new naphthalene derivatives of the general formula (I) are obtained when (a) corresponding carbonyl compounds of the general formula (II)

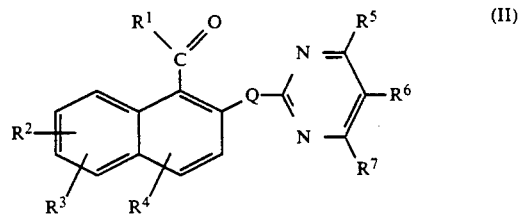

in which Q, $R^1$, $R^2$, $R^3$, $R^4$, $R^5$, $R^6$ and $R^7$ have the abovementioned meanings, are reacted with amino compounds or methylene compounds of the general formula (III)

$$H_2Z \qquad (III)$$

in which Z has the abovementioned meaning, if appropriate in the presence of a reaction auxiliary and if appropriate in the presence of a diluent, or when (b) nucleophilic naphthalene derivatives of the general formula (IV)

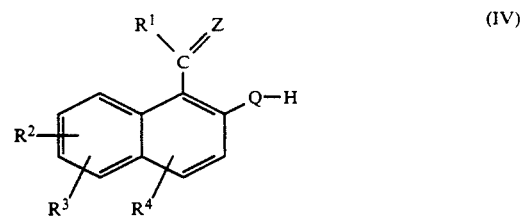

in which Q, $R^1$, $R^2$, $R^3$, $R^4$ and Z have the abovementioned meanings, are reacted with pyrimidine derivatives of the general formula (V)

in which $R^5$, $R^6$ and $R^7$ have the abovementioned meanings and

X represents a nucleofugic leaving group, if appropriate in the presence of an acid acceptor and if appropriate in the presence of a diluent.

The new naphthalene derivatives of the general formula (I) are distinguished by a powerful herbicidal action.

Surprisingly, the naphthalene derivatives of the formula (I) according to the invention have a considerably more powerful action against weeds than the compound 2-(4,6-dimethoxy-pyrimidin-2-yl-oxy)-1-naphthaldehyde, which has been disclosed and is a previously known active compound of similar structure and the same direction of action, and they also show good compatibility with important crop plants.

The invention preferably relates to compounds of the formula (I)
in which
Q represents oxygen, sulphur or the group NR, where R represents hydrogen or $C_1$–$C_4$-alkyl,
$R^1$ represents hydrogen or $C_1$–$C_4$-alkyl,
$R^2$, $R^3$ and $R^4$ are identical or different and in each case represent hydrogen, hydroxyl, amino, cyano, nitro or halogen, or represent $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl each of which is optionally substituted by halogen,
$R^5$ represents hydrogen or halogen, or represents $C_1$–$C_4$-alkyl, $C_1$–$C_4$-alkoxy, $C_1$–$C_4$-alkylthio, $C_1$–$C_4$-alkylamino or di-($C_1$–$C_4$-alkyl)-amino each of which is optionally substituted by halogen or $C_1$–$C_4$-alkoxy,
$R^6$ represents hydrogen or halogen, or represents $C_1$–$C_4$-alkyl, or $C_1$–$C_4$-alkoxy in each case optionally substituted by halogen,
$R^7$ represents hydrogen or halogen, or represents $C_1$–$C_4$-alkyl, $C_1$–$C_4$-alkoxy, $C_1$–$C_4$-alkylthio, $C_1$–$C_4$-alkylamino or di-($C_1$–$C_4$-alkyl)-amino, each of which is optionally substituted by halogen,
Z represents one of the following groups: N—$R^8$ or

where
$R^8$ represents hydrogen, hydroxyl, amino or carbamoylamino, or represents $C_1$–$C_6$-alkyl, $C_3$–$C_6$-alkenyl, $C_3$–$C_6$-alkinyl, $C_1$–$C_6$-alkoxy, $C_3$–$C_6$-alkenyloxy, $C_1$–$C_4$-alkoxy-carbonyl-$C_1$–$C_2$-alkoxy, $C_1$–$C_6$-alkylamino, di-($C_1$–$C_{24}$-alkyl)-amino, $C_1$–$C_6$-alkylcarbonylamino, $C_1$–$C_6$-alkoxycarbonylamino or $C_1$–$C_6$-alkylsulphonylamino, each of which is optionally substituted by halogen, or represents phenyl, phenyl-$C_1$–$C_4$-alkyl, phenoxy, phenyl-$C_1$–$C_4$-alkoxy, phenylamino, diphenylamino, phenyl-$C_1$–$C_4$-alkylamino, N-($C_1$–$C_4$-alkyl)-N-phenylamino, pyridylamino, pyrimidylamino, quinolylamino, pyridylcarbonylamino, phenylcarbonylamino, furylcarbonylamino, thienylcarbonylamino or phenylsulphonylamino each of which is optionally substituted by nitro, hydroxyl, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxycarbonyl and/or di-($C_1$–$C_2$-alkyl)-amino,
$R^9$ represents hydrogen, halogen, cyano, carboxyl, $C_1$–$C_6$-alkoxycarbonyl, $C_1$–$C_6$-alkylcarbonylamino or di-($C_1$–$C_4$-alkoxy)-phosphoryl, and
$R^{10}$ represents formyl, cyano, carboxyl, hydroxymethyl or carbamoyl, or represents $C_1$–$C_6$-alkoxycarbonyl, $C_5$–$C_6$-cycloalkyloxycarbonyl, $C_1$–$C_6$-alkylthiocarbonyl, $C_1$–$C_6$-alkylaminocarbonyl or $C_5$–$C_6$-cycloalkylaminocarbonyl each of which is optionally substituted by halogen, carboxyl or $C_1$–$C_4$-alkoxycarbonyl, or represents di-$C_1$–$C_2$-alkyl)-aminocarbonyl, or represents $C_1$–$C_4$-alkylaminocarbonyl-$C_1$–$C_4$-alkoxycarbonyl, or represents di-(-$C_1$–$C_2$-alkyl)-aminocarbonyl-$C_1$–$C_4$-alkoxycarbonyl, or represents phenylaminocarbonyl-$C_1$–$C_4$-alkoxycarbonyl, or represents N-methyl-N-phenyl-aminocarbonyl-$C_1$–$C_4$-alkoxycarbonyl, or represents pyrrolidinylcarbonyl, piperidinylcarbonyl, morpholinylcarbonyl or piperazinylcarbonyl each of which is optionally substituted by methyl and/or ethyl, or represents phenoxycarbonyl, phenyl-$C_1$–$C_4$-alkoxycarbonyl, furylmethoxycarbonyl, thienylmethoxycarbonyl, phenylthiocarbonyl, phenyl-$C_1$–$C_4$-alkylthiocarbonyl, phenylaminocarbonyl, phenyl-$C_1$–$C_4$-alkylaminocarbonyl, N-($C_1$–$C_4$-alkyl)-N-phenylaminocarbonyl or phenylhydrazinocarbonyl, each of which is optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxycarbonyl and/or di-($C_1$–$C_2$-alkyl)-amino, or represents $C_1$–$C_4$-alkylhydrazinocarbonyl or phthalimidoxycarbonyl, or $R^{10}$ together with $R^9$ represents the group —CO—O—$(CH_2)_n$— where
n represents the numbers 1 to 4, in particular 2 or 3.

The aliphatic hydrocarbon radicals listed in the definition of the compounds according to the invention (for example alkyl, alkenyl, alkynyl) are in each case straight-chain or branched, also in combination with hetero atoms (for example in alkoxy, alkylthio, alkylamino) or in combinations such as, for example, halogenoalkyl or halogenoalkoxy.

Halogen generally represents fluorine, chlorine, bromine or iodine, preferably fluorine, chlorine or bromine, in particular fluorine or chlorine.

The invention particularly relates to compounds of the formula (I)
in which
Q represents oxygen,
$R^1$ represents hydrogen,
$R^2$, $R^3$ and $R^4$ represent hydrogen,
$R^5$ represents hydrogen, chlorine, methyl, ethyl, trifluoromethyl, methoxymethyl, methoxy, ethoxy, difluoromethoxy, methylthio, methylamino, ethylamino or dimethylamino, in particular methoxy,
$R^6$ represents hydrogen, chlorine, methyl or methoxy, in particular hydrogen, and
$R^7$ represents hydrogen, chlorine, methyl, ethyl, trifluoromethyl, methoxy, ethoxy, difluoromethoxy, methylthio, methylamino, ethylamino or dimethylamino, in particular methoxy, and
Z represents one of the following groups: N—$R^8$ or

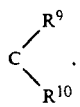

where

R[8] represents hydrogen, hydroxyl, amino or carbamoylamino, or represents methyl, ethyl, n-propyl, isopropyl, n-butyl, isobutyl, sec-butyl, tert-butyl, allyl, propargyl, methoxy, ethoxy, n-propoxy, isopropoxy, n-butoxy, isobutoxy, sec-butoxy, allyloxy, methoxycarbonylmethoxy, ethoxycarbonylmethoxy, methoxycarbonylethoxy, ethoxycarbonylethoxy, ethylamino, n-propylamino, isopropylamino, n-butylamino, isobutylamino, sec-butylamino, tert-butylamino, dimethylamino, acetylamino, propionylamino, methoxycarbonylamino, ethoxycarbonylamino, methylsulphonylamino or ethylsulphonylamino, or represents phenyl, benzyl, phenoxy, benzyloxy, phenylamino, diphenylamino, benzylamino, N-methyl-N-phenylamino, pyridylamino, pyrimidylamino, quinolylamino, pyridylcarbonylamino, phenylcarbonylamino, furylcarbonylamino, thienylcarbonylamino or phenylsulphonylamino each of which is optionally substituted by nitro, hydroxyl, cyano, carboxyl, fluorine, chlorine, bromine, methyl, trifluoromethyl, methoxy, trifluoromethoxy, methylthio or trifluoromethylthio, R[9] represents hydrogen, fluorine, chlorine, cyano, carboxyl, $C_1$-$C_4$-alkoxycarbonyl, $C_1$-$C_4$-alkylcarbonylamino, dimethoxyphosphoryl or diethoxyphosphoryl, and R[10] represents formyl, cyano, carboxyl, hydroxymethyl or carbamoyl, or represents $C_1$-$C_4$-alkoxycarbonyl, $C_5$-$C_6$-cycloalkyloxycarbonyl, $C_1$-$C_4$-alkylthiocarbonyl, $C_1$-$C_4$-alkylaminocarbonyl or $C_5$-$C_6$-cycloalkylaminocarbonyl each of which is optionally substituted by fluorine, chlorine, carboxyl or $C_1$-$C_4$-alkoxycarbonyl, or represents dimethylaminocarbonyl, or represents $C_1$-$C_4$-alkylaminocarbonyl-$C_1$-$C_4$-alkoxycarbonyl, or represents dimethylaminocarbonyl-$C_1$-$C_4$-alkoxycarbonyl, represents N-methyl-N-phenylaminocarbonyl-$C_1$-$C_4$-alkoxycarbonyl, or represents pyrrolidinylcarbonyl, piperidinylcarbonyl, morpholinylcarbonyl or piperazinylcarbonyl each of which is optionally substituted by methyl and/or ethyl, or represents phenoxycarbonyl, benzyloxycarbonyl, phenylthiocarbonyl, benzylthiocarbonyl, phenylaminocarbonyl, benzylaminocarbonyl, N-methyl-N-phenylaminocarbonyl or phenylhydrazinocarbonyl each of which is optionally substituted by nitro, cyano, fluorine, chlorine, bromine, methyl, trifluoromethyl, methoxy, trifluoromethoxy, methylthio or trifluoromethylthio, or represents phthalimidoxycarbonyl, or R[10] together with R[9] represents the group —CO—O—CH$_2$CH$_2$—.

If, for example, 2-(4,6-dimethoxypyrimidin-2-yl-oxy)-1-naphthaldehyde and acetohydrazide are used as starting substances in process (a) according to the invention, the course of the reaction can be outlined by the following equation:

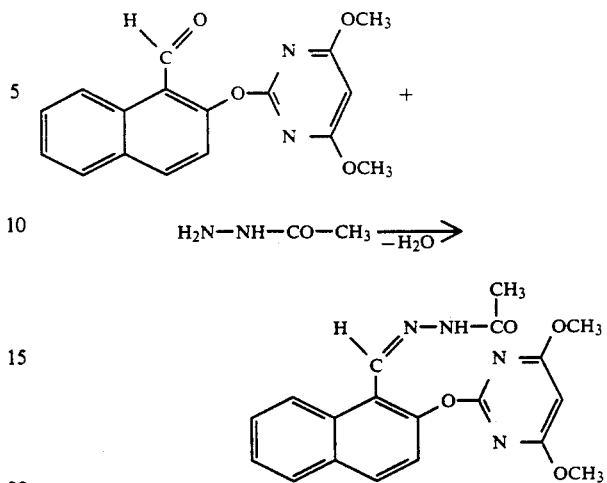

If, for example, 1-methoximinomethyl-2-naphthol and 2-chloro-4,6-dimethoxypyrimidine are used as starting substances in process (b) according to the invention, the course of the reaction can be outlined by the following equation:

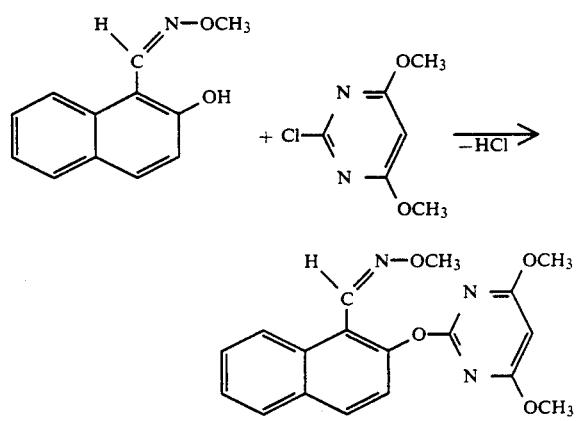

Formula (II) provides a general definition of the carbonyl compounds to be used as starting substances in process (a) according to the invention for the preparation of compounds of the formula (I).

In formula (II), Q, R[1], R[2], R[3], R[4], R[5], R[6] and R[7] preferably, or in particular, have those meanings which have already been mentioned above in connection with the description of the compounds of the formula (I) according to the invention as being preferred, or as particularly preferred, for Q, R[1], R[2], R[3], R[4], R[5], R[6] and R[7].

Examples of the starting substances of the formula (II) which may be mentioned are: 2-(4,6-dimethoxypyrimidin-2-yl-oxy)-, 2-(4-methoxy-6-methylpyrimidin-2-yl-oxy)-, 2-(4,6-dimethylpyrimidin-2-yl-oxy)-, 2-(4-methoxy-6-trifluoromethylpyrimidin-2-yl- oxy)-, 2-(4-ethyl-6-methoxypyrimidin-2-yl-oxy)-, 2-(4-ethoxy-6-methylpyrimidin-2-yl-oxy)- and 2-(4,6-diethoxy-pyrimidin-2-yl-oxy)-1-naphthaldehyde.

The carbonyl compounds of the formula (II) are known and/or can be prepared by processes known per se (cf. EP-A 360,163; JP-A 2,056,469—cited in Chem. Abstracts 113 (1990), 54345m; Preparation Examples).

Formula (III) provides a general definition of the amino compounds or methylene compounds furthermore to be used as starting substances in process (a) according to the invention for the preparation of compounds of the formula (I).

In formula (III), Z preferably, or in particular, has the meaning which has already been mentioned above in connection with the description of the compounds of the formula (I) according to the invention as being preferred, or as particularly preferred, for Z.

Examples of the starting substances of the formula (III) which may be mentioned are: ammonia, hydroxylamine, hydrazine, methylamine, ethylamine, propylamine, isopropylamine, butylamine, isobutylamine, sec-butylamine, tert-butylamine, allylamine, propargylamine, O-methyl-, O-ethyl-, O-propyl-, O-isopropyl-, O-butyl-, O-isobutyl- and O-sec-butyl-hydroxylamine, O-allyl-hydroxylamine, methyl aminooxyacetate and ethyl aminooxyacetate, methyl α-aminooxypropionate and ethyl α-aminooxypropionate, methylhydrazine, ethylhydrazine, propylhydrazine, isopropylhydrazine, butylhydrazine, isobutylhydrazine, sec-butyl-hydrazine, tertbutylhydrazine, N,N-dimethylhydrazine, acetohydrazide, propionylhydrazide, methoxycarbonylhydrazine, ethoxycarbonylhydrazine, methylsulphonylhydrazine, ethylsulphonylhydrazine, phenylhydrazine, benzoylhydrazine, benzene sulphohydrazide, p-toluenesulphohydrazide, malonic acid, cyanoacetic acid, malodinitrile, methyl cyanoacetate and ethyl cyanoacetate, dimethyl malonate and diethyl malonate, and γ-butyrolactone.

The starting substances of the formula (III) are known chemicals for synthesis.

Process (a) according to the invention for the preparation of the new naphthalene derivatives of the formula (I) is preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulphoxide, tetramethylene sulphone and hexamethylphosphoric triamide.

If appropriate, process (a) according to the invention is carried out in the presence of a reaction auxiliary. Suitable reaction auxiliaries are substances which are customarily used for controlling and/or accelerating condensation reactions between carbonyl compounds and amino compounds or methylene compounds. These include, in particular, nitrogen compounds such as, for example, ammonium acetate, β-alanine, pyridine and piperidine.

When carrying out process (a) according to the invention, the reaction temperatures can be varied within a substantial range. In general, the process is carried out at temperatures between 0° C. and 150° C., preferably at temperatures between 10° C. and 120° C.

Process (a) according to the invention is generally carried out under atmospheric pressure However, it is also possible to carry out the process under increased or reduced pressure.

For carrying out process (a) according to the invention, the starting substances required in each case are generally employed in approximately equimolar amounts. However, it is also possible to use one of the two components employed in each case in a larger excess. In general, the reactions are carried out in a suitable diluent, if appropriate in the presence of a reaction auxiliary, and the reaction mixture is stirred for several hours at the specific temperature required. Working-up in the process according to the invention is carried out in each case by customary methods (compare the preparation examples).

Formula (IV) provides a general definition of the nucleophilic naphthalene derivatives to be used as starting substances in process (b) according to the invention for the preparation of compounds of the formula (I).

In formula (IV), Q, $R^1$, $R^2$, $R^3$, $R^4$ and Z preferably, or in particular, have those meanings which have already been mentioned above in connection with the description of the compounds of the formula (I) according to the invention as being preferred, or particularly preferred, for Q, $R^1$, $R^2$, $R^3$, $R^4$ and Z.

Examples of the starting substances of the formula (IV) are listed in Table 1 below.

TABLE 1

Examples of the starting substances of the formula (IV)

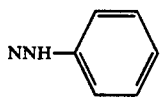

(IV)

| Q | $R^1$ | $R^2$ | $R^3$ | $R^4$ | Z |
|---|---|---|---|---|---|
| O | H | H | H | H | $NOCH_3$ |
| O | H | H | H | H | $NOC_2H_5$ |
| O | H | H | H | H | $NCH_3$ |
| O | H | H | H | H | $NC_2H_5$ |
| O | H | H | H | H | $NCH(CH_3)_2$ |
| O | H | H | H | H | $NOCH_2COOC_2H_5$ |
| O | H | H | H | H | $NCH_2COOC_2H_5$ |
| O | H | H | H | H | $NNHCOCH_3$ |
| O | H | H | H | H | $NNHSO_2CH_3$ |
| O | H | H | H | H | $NNHCOOCH_3$ |
| O | H | H | H | H | NNH—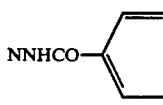 |
| O | H | H | H | H | NNHCO—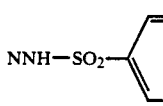 |
| O | H | H | H | H | NNH—$SO_2$—⌬ |

TABLE 1-continued

Examples of the starting substances of the formula (IV)

R¹\\\\Z
  C
 /  \\
(naphthalene)—Q—H
R²—
R³  R⁴

(IV)

| Q | R¹ | R² | R³ | R⁴ | Z |
|---|----|----|----|----|---|
| O | H | H | H | H | NNH—(2-pyridyl) |
| O | H | H | H | H | NNH—CO—(2-pyridyl) |
| O | H | H | H | H | NOCH₂—phenyl |
| O | H | H | H | H | NNH—CO—(2-furyl) |
| O | H | H | H | H | NNH—(2-pyrimidyl) |
| O | H | H | H | H | NN(CH₃)—phenyl |
| O | H | H | H | H | NNH—(4-fluorophenyl) |

The starting substances of the formula (IV) are known and/or can be prepared by processes known per se (cf. Synthesis 1985, 201–202; U.S. Pat. No. 4,277,500; Tetrahedron Lett. 1975, 785–788; Chem. Pharm. Bull. 24 (1976), 3065–3074; U.S. Pat. No. 4,334,015; Preparation Examples).

Formula (V) provides a general definition of the pyrimidine derivatives furthermore to be used as starting substances in process (b) according to the invention for the preparation of compounds of the formula (I).

In formula (V), $R^5$, $R^6$ and $R^7$ preferably, or in particular, have those meanings which have already been mentioned above in connection with the description of the compounds of the formula (I) according to the invention as being preferred, or as particularly preferred, for $R^5$, $R^6$ and $R^7$ and X preferably represents fluorine, chlorine, bromine or $C_1$–$C_4$-alkylsulphonyl, in particular chlorine or methylsulphonyl.

Examples of the starting substances of the formula (V) which may be mentioned are: 2-chloro- and 2-methylsulphonyl-4,6-dimethylpyrimidine, -4-methyl-6-methoxypyrimidine, -4,6-dimethoxypyrimidine, -4-methyl-6-ethoxypyrimidine, -4-chloro-6-methoxypyrimidine, -4-methylpyrimidine -4-chloro-6-methylpyrimidine, -4-trifluoromethyl-6-methoxypyrimidine-, -4-methoxy-6-difluoromethoxypyrimidine, -4-methyl-6-difluoromethoxypyrimidine, -4,6-bis-difluoromethoxypyrimidine, -4-chloro-6-ethoxypyrimidine, -4,6-diethoxypyrimidine, -4,5-dichloro-6-methylpyrimidine, -4-methyl-5-chloro-6-methoxypyrimidine, -4,6-dichloropyrimidine, -4-ethyl-6-methoxypyrimidine, -5-chloro-4,6-dimethoxypyrimidine, -4-methoxy-6-methylaminopyrimidine, and also -4,6-bis-trifluoromethylpyrimidine.

The pyrimidine derivatives of the formula (V) are known and/or can be prepared by processes known per se (cf. J. Chem. Soc. 1957, 1830, 1833; J. Org. Chem. 26 (1961), 792; U.S. Pat. No. 3,308,119 and U.S. Pat. No. 4,711,959).

Process (b) according to the invention for the preparation of the new naphthalene derivatives of the formula (I) is preferably carried out using diluents.

Diluents which are suitable for this purpose are virtually all inert organic solvents These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in process (b) according to the invention are all acid-binding agents which can customarily be employed for reactions of this type. The following are preferably suitable: alkali metal hydroxides such as, for example, sodium hydroxide and potassium hydroxide, alkaline earth metal hydroxides such as, for example, calcium hydroxide, alkali metal carbonates and alkali metal alcoholates such as sodium carbonate and potassium carbonate, sodium tert-butylate and potassium tert-butylate, furthermore aliphatic, or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

When carrying out the process (b) according to the invention, the reaction temperatures can be varied within a substantial range. In general, the process is carried out at temperatures between 0° C. and 150° C., preferably at temperatures between 10° C. and 100° C.

Process (b) according to the invention is generally carried out under atmospheric pressure. However, it is also possible to carry out the process under increased or reduced pressure.

For carrying out process (b) according to the invention, the starting substances required in each case are generally employed in approximately equimolar amounts. However, it is also possible to use one of the two components employed in each case in a larger excess. In general, the reactions are carried out in a suitable diluent in the presence of an acid acceptor, and the reaction mixture is stirred for several hours at the particular temperature required. Working-up in process (b) according to the invention is carried out in each case by customary methods (cf. the Preparation Examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chemopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucmis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and on lawns, turf and pasture-land, and for the selective combating of weeds in annual cultures.

The compounds of the formula (I) according to the invention are particularly suitable for selectively combating monocotyledon and dicotyledon weeds in monocotyledon and dicotyledon crops, both pre-emergence and post-emergence.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, choloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolmite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumi n hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine -2,4-(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBU-ZIN) for combating weeds in soy beans. Furthermore also 2,4-dichlorophenoxyacetic acid (2,4-D); 4-(2,4-dichlorophenoxy)-butric acid (2,4-DB); 2,4- dichlorophenoxypropionic acid (2,4-DP); 2',6'-diethyl-N-methoxymethylchloroacetanilide (ALACHLOR); methyl-6,6-dimethyl-2,4-dioxo-3-[1-(2-propenyloxyamino)-butylidene]-cyclohexanecarboxylic acid (ALLOXYDIM); 2-chloro-4-ethylamino-6-isopropylamino-1,3,5-triazine (ATRAZINE); 3-isopropyl-2,1,3-benzothiadiazin-4-one 2,2-dioxide (BENTAZONE); 3,5-dibromo-4-hydroxy-benzonitrile (BROMOXYNIL); N-(3-chlorophenyl)-isopropyl carbamate (CHLORPROPHAM); 2-chloro-N-{[(4-methoxy-6-methyl-1,3,5-triazin-2-yl)amino]carbonyl}-benzenesulphonamide (CHLORSULFURON); N,N-dimethyl-N'-(3-chloro-4-methyl-phenyl)-urea (CHLORTOLURON); exo-1-methyl-4-(1-methyl-ethyl)-2-(2-methylphenyl-methoxy)-7- oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); 2-[1-(ethoximino)butyl]-3-hydroxy-5-[tetrahydro-2H)-thiopyran-3-yl]-2-cyclohexen-1-one (CYCLOXYDIM); 2-[4-(2,4-dichlorophenoxy)-phenoxy]-propionic acid, its methyl ester or its ethyl ester (DICLOFOP); 2-[(2-chlorophenyl)-methyl]-4,4-dimethylisoxazolidin-3-one (DIMETHAZONE); S-ethyl N,N-di-n-propyl-thiocarbamidate (EPTAME); 4-amino-6-t-butyl-3- ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-pryidyloxy)-phenoxy]-propanoic acid or its butyl ester (FLUAZIFOP); [(4-amino-3,5-dichloro-6-fluoro-2-pyridinyl)-oxy]-acetic acid or its 1-methyl-heptyl ester (FLUROXYPYR); 2-{4-[(3-chloro-5-(trifluoro-methyl)-2-pyridinyl)-oxy]-phenoxy}-propanoic acid or its ethyl ester (HALOXYFOP); 3-cyclohexyl-6-dimethylamino-1-methyl-1,3,5-triazine-2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-ylmethyl]-acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); isopropyl N-phenyl carbamate (PROPHAM); O-(6-chloro-3-phenyl-pyridazin-4-yl) S-octyl thiocarbonate (PYRIDATE); ethyl 2-[4-(6-chloro-quinoxalin-2-yl-oxy)-phenoxy]-propionate (QUIZALOFOPETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-[(4-chloro-phenyl)-methyl] N,N-diethylthiocarbamate (THIOBENCARB); S-(2,3,3-trichloroallyl-) N,N-diisopropylthiocarbamate (TRI-ALLATE); and 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

Example 1

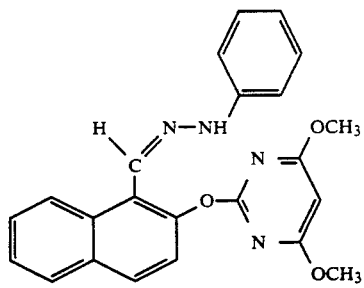

Process (a)

A mixture of 3.1 g (10 mmol) of 2-(4,6-dimethoxy-pyrimidin-2-yl-oxy)-1-naphthaldehyde, 1.2 g (10 mmol) of phenylhydrazine and 40 ml of toluene is stirred at 20° C. and subsequently concentrated. The residue is brought to crystallisation using ethanol, and the crystalline product is isolated by filtration with suction.

2.2 g (55% of theory) of 2-(4,6-dimethoxypyrimidin-2-yl-oxy)-1-naphthaldehyde phenylhydrazone of melting point 148° C. are obtained.

EXAMPLE 2

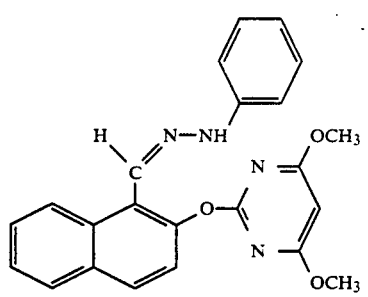

Process (b)

2-Hydroxy-1-naphthaldehyde phenylhydrazone (2.6 g, 10 mmol) and potassium carbonate (1.4 g) are added to 4,6-dimethoxy-2-methylsulphonylpyrimidine (2.2 g, 10 mmol) in acetonitrile (50 ml). The mixture is refluxed for 7 hours, poured into ice-water and extracted with diethyl ether. The extract is dried over sodium sulphate and then concentrated.

3.1 g (76% of theory) of 2-(4,6-dimethoxypyrimidin-2-yl-oxy)-1-naphthaldehyde phenylhydrazone of melting point 148° C. are obtained.

Other examples of the compounds of the formula (I) which can be prepared analogously to Examples 1 and 2 and corresponding to the general description of the preparation processes according to the invention are those listed in Table 2 below.

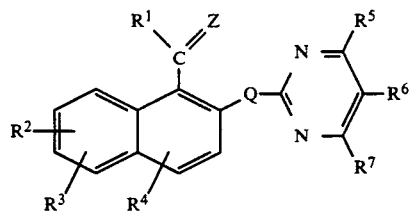

TABLE 2

Examples of the compounds of the formula (I)

| Example no. | Q | $R^1$ | $R^2$ | $R^3$ | $R^4$ | $R^5$ | $R^6$ | $R^7$ | Z | Melting point (°C.) |
|---|---|---|---|---|---|---|---|---|---|---|
| 3 | O | H | H | H | H | $OCH_3$ | H | $OCH_3$ | (methylene-γ-butyrolactone group) | 129 |
| 4 | O | H | H | H | H | $OCH_3$ | H | $OCH_3$ | CHCOOH | (amorphous) |
| 5 | O | H | H | H | H | $OCH_3$ | H | $OCH_3$ | $NNHCH_3$ | (amorphous) |
| 6 | O | H | H | H | H | $OCH_3$ | H | $OCH_3$ | $C(CN)_2$ | 118 |
| 7 | O | H | H | H | H | $OCH_3$ | H | $OCH_3$ | C(CN)(COOH) | 134 |
| 8 | O | H | H | H | H | $OCH_3$ | H | $OCH_3$ | NNH-(2,4-difluorophenyl) | 171 |
| 9 | O | H | H | H | H | $OCH_3$ | H | $OCH_3$ | NNH-(4-trifluoromethylphenyl) | 170 |
| 10 | O | H | H | H | H | $OCH_3$ | H | $OCH_3$ | NNH-(4-fluorophenyl) | 145 |
| 11 | O | H | H | H | H | $OCH_3$ | H | $OCH_3$ | NNH-(3-chloro-4-fluorophenyl) | 187 |
| 12 | O | H | H | H | H | $OCH_3$ | H | $OCH_3$ | NNH-(3-methylphenyl) | (amorphous) |

TABLE 2-continued
Examples of the compounds of the formula (I)
| Example no. | Q | R¹ | R² | R³ | R⁴ | R⁵ | R⁶ | R⁷ | Z | Melting point (°C.) |
|---|---|---|---|---|---|---|---|---|---|---|
| 13 | O | H | H | H | H | OCH₃ | H | OCH₃ | 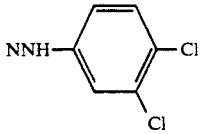 | 174 |
| 14 | O | H | H | H | H | OCH₃ | H | OCH₃ | 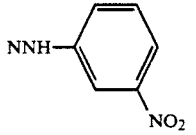 | 185 |
| 15 | O | H | H | H | H | OCH₃ | H | OCH₃ | 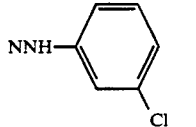 | 171 |
| 16 | O | H | H | H | H | OCH₃ | H | OCH₃ | 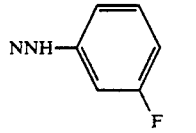 | 149 |
| 17 | O | H | H | H | H | OCH₃ | H | OCH₃ | 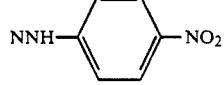 | 235 |
| 18 | O | H | H | H | H | OCH₃ | H | OCH₃ | 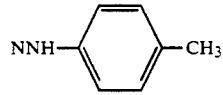 | 123 |
| 19 | O | H | H | H | H | OCH₃ | H | OCH₃ | 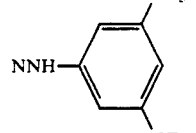 | 178 |
| 20 | O | H | H | H | H | OCH₃ | H | OCH₃ | 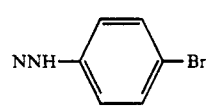 | 141 |
| 21 | O | H | H | H | H | OCH₃ | H | OCH₃ | 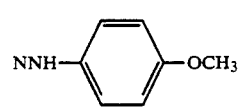 | 141 |
| 22 | O | H | H | H | H | OCH₃ | H | OCH₃ | 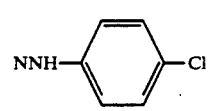 | 147 |
| 23 | O | H | H | H | H | OCH₃ | H | OCH₃ | 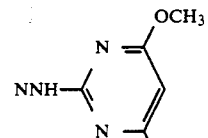 | 160 |

TABLE 2-continued

Examples of the compounds of the formula (I)

| Example no. | Q | R¹ | R² | R³ | R⁴ | R⁵ | R⁶ | R⁷ | Z | Melting point (°C.) |
|---|---|---|---|---|---|---|---|---|---|---|
| 24 | O | H | H | H | H | OCH₃ | H | OCH₃ | NN(CH₃)(C₆H₅) | (amorphous) |
| 25 | O | H | H | H | H | OCH₃ | H | OCH₃ | NNHSO₂-(3-CF₃-C₆H₄) | 168 |
| 26 | O | H | H | H | H | OCH₃ | H | OCH₃ | NNHSO₂-(3-Cl-C₆H₄) | 175 |
| 27 | O | H | H | H | H | OCH₃ | H | OCH₃ | NNHSO₂-(4-OCH₃-C₆H₄) | 145 |
| 28 | O | H | H | H | H | OCH₃ | H | OCH₃ | NNHSO₂-(3-OCF₃-C₆H₄) | 129 |
| 29 | O | H | H | H | H | OCH₃ | H | OCH₃ | NNHSO₂-(3-CF₂Cl-C₆H₄) | 112 |
| 30 | O | H | H | H | H | OCH₃ | H | OCH₃ | NNHSO₂-(3-OC₄H₉-n-C₆H₄) | 134 |
| 31 | O | H | H | H | H | OCH₃ | H | OCH₃ | NN(C₆H₅)₂ | 92 |
| 32 | O | H | H | H | H | OCH₃ | H | OCH₃ | NOCH(CH₃)COOCH₃ | (amorphous) |
| 33 | O | H | H | H | H | OCH₃ | H | OCH₃ | NNHSO₂CH₃ | 134 |
| 34 | O | H | H | H | H | OCH₃ | H | OCH₃ | NNH-(7-Cl-quinolin-4-yl) | 196 |
| 35 | O | H | H | H | H | OCH₃ | H | OCH₃ | NNHSO₂-C₆H₅ | 65 |
| 36 | O | H | H | H | H | OCH₃ | H | OCH₃ | NOCH₂COOC₂H₅ | (amorphous) |

TABLE 2-continued

Examples of the compounds of the formula (I)

| Example no. | Q | R¹ | R² | R³ | R⁴ | R⁵ | R⁶ | R⁷ | Z | Melting point (°C.) |
|---|---|---|---|---|---|---|---|---|---|---|
| 37 | O | H | H | H | H | OCH₃ | H | OCH₃ | NNHSO₂—C₆H₄—CH₃ (para) | 170 |
| 38 | O | H | H | H | H | OCH₃ | H | OCH₃ | NNHCOCH₃ | 205 |
| 39 | O | H | H | H | H | OCH₃ | H | OCH₃ | NNHCO—C₆H₅ | 179 |
| 40 | O | H | H | H | H | OCH₃ | H | OCH₃ | NNHCO—C₆H₄—OH (para) | 215 |
| 41 | O | H | H | H | H | OCH₃ | H | OCH₃ | NNH—C₆H₄—COOH (para) | 240 |
| 42 | O | H | H | H | H | OCH₃ | H | OCH₃ | NNH—C₆H₃(F)(F) (3,4-difluoro) | 174 |
| 43 | O | H | H | H | H | OCH₃ | H | OCH₃ | NNH—C₆H₄—Cl (ortho) | 161 |
| 44 | O | H | H | H | H | OCH₃ | H | OCH₃ | NN(CH(CH₃)₂)—C₆H₅ | 113 |
| 45 | O | H | H | H | H | OCH₃ | H | OCH₃ | NNH—(3-CF₃, 5-Cl-pyridin-2-yl) | 214 |
| 46 | O | H | H | H | H | OCH₃ | H | OCH₃ | NNHCONH₂ | 216 |
| 47 | O | H | H | H | H | OCH₃ | H | OCH₃ | NNH—C₆H₄—COOH (ortho) | 219 |
| 48 | O | H | H | H | H | OCH₃ | H | OCH₃ | NNH—(pyridin-2-yl) | 142 |
| 49 | O | H | H | H | H | OCH₃ | H | OCH₃ | NNH—C₆H₄—CN (para) | 224 |

TABLE 2-continued

Examples of the compounds of the formula (I)

| Example no. | Q | $R^1$ | $R^2$ | $R^3$ | $R^4$ | $R^5$ | $R^6$ | $R^7$ | Z | Melting point (°C.) |
|---|---|---|---|---|---|---|---|---|---|---|
| 50 | O | H | H | H | H | OCH$_3$ | H | OCH$_3$ | NN(CH(CH$_3$)C$_2$H$_5$)(C$_6$H$_5$) | 89 |
| 51 | O | H | H | H | H | OCH$_3$ | H | OCH$_3$ | NN(CH(CH$_3$)$_2$)—C$_6$H$_4$—Cl | 95 |
| 52 | O | H | H | H | H | OCH$_3$ | H | OCH$_3$ | NNH—C$_6$H$_4$—C(CH$_3$)$_3$ | (amorphous) |

STARTING SUBSTANCES OF THE FORMULA (II)

Example (II-1)

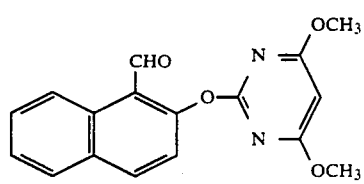

2-Hydroxy-1-naphthaldehyde (5.1 g, 90 mmol) and potassium carbonate (8.3 g) are added to 4,6-dimethoxy-2-methylsulphonylpyrimidine (6.5 g, 90 mmol) in acetonitrile (100 ml). The mixture is refluxed for 18 hours, poured into ice-water and extracted with diethyl ether. The extract is dried over sodium sulphate and then concentrated. The substance which remains is purified by chromatography on silica gel.

4.7 g (50% of theory) of 2-(4,6-dimethoxy-pyrimidin-2-yl-oxy)-1-naphthaldehyde of melting point 135° C. are obtained.

STARTING SUBSTANCES OF THE FORMULA (IV)

Example (IV-1)

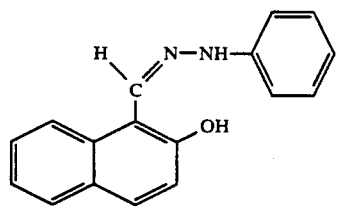

Phenylhydrazine (5.4 g, 50 mmol) is added to 2-hydroxy-1-naphthaldehyde (8.6 g, 50 mmol) in toluene (70 ml), and stirring is continued for 1 hour at 20° C. The crystalline product is isolated by filtration with suction.

2-Hydroxy-1-naphthaldehyde phenylhydrazone (9.6 g, 73 % of theory) of melting point 210° C. (decomposition) is obtained.

USE EXAMPLES

In the use examples, the compound (A) outlined below is used as comparison substance:

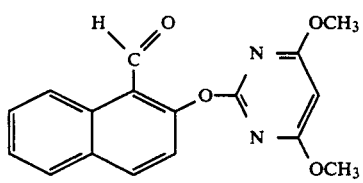

2-(4,6-dimethoxy-pyrimidin-2-yl-oxy)-1-naphthaldehyde (disclosed in EP-A 360,163 and JP-A 2,056,469).

Example A

Post-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 1 of water/ha. After three weeks, the degree of damage to the plants is rated in % damage in comparison to the development of the untreated control. The figures denote:

0% = no action (like untreated control)

100% = total destruction

In this test, a clearly superior activity and selectivity towards crop plants compared with the prior art is shown, for example, by the compounds of the following preparation examples: 1, 8, 9, 10, 11, 12, 13, 14, 15, 16, 19, 21, 27, 28, 31 and 33.

Example B

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, a clearly superior activity and selectivity towards crop plants compared with the prior art is shown, for example, by the compounds of the following preparation examples: 1, 7, 8, 9, 10, 12, 13, 14, 15, 16, 19, 20, 21, 22, 24, 25, 26, 27, 29, 30, 31 and 33.

It will be understood that the specification and examples are illustrative but not limitative of the present invention and that other embodiments within the spirit and scope of the invention will suggest themselves to those skilled in the art.

We claim:

1. A naphthalene derivative of the formula

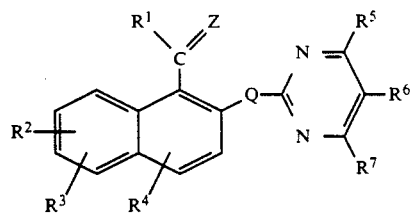

in which

Q represents oxygen, $R^1$ represents hydrogen, $R^2$, $R^3$ and $R^4$ represent hydrogen, halogen or methoxy, $R^5$ represents hydrogen, chlorine, methyl, ethyl, trifluoromethyl, methoxymethyl, methoxy, ethoxy, difluoromethoxy, methylthio, methylamino, ethylamino or dimethylamino, $R^6$ represents hydrogen, chlorine, methyl or methoxy, $R^7$ represents hydrogen, chlorine, methyl, ethyl, trifluoromethyl, methoxy, ethoxy, difluoromethoxy, methylthio, methylamino, ethylamino or dimethylamino, Z represents N—$R^8$ or

$R^8$ represents hydrogen, amino or carbamoylamino, or represents methyl, ethyl, n-propyl, isopropyl, n-butyl, isobutyl, sec-butyl, tert-butyl, allyl, propargyl, methylamino, ethylamino, n-propylamino, isopropylamino, n-butylamino, isobutylamino, sec-butylamino, tert-butylamino, dimethylamino, acetylamino, propionylamino, methoxycarbonylamino, ethoxycarbonylamino, methylsulphonylamino or ethylsulphonylamino, or represents phenyl, benzyl, phenylamino, diphenylamino, benzylamino, N-methyl-N-phenylamino, pyridylamino, pyrimidylamino, quinolylamino, pyridylcarbonylamino, phenylcarbonylamino, furylcarbonylamino, thienylcarbonylamino or phenylsulphonylamino each of which is optionally substituted by nitro, hydroxyl, cyano, carboxyl, fluorine, chlorine, bromine, methyl, trifluoromethyl, methoxy, trifluoromethoxy, methylthio or trifluoromethylthio, $R^9$ represents hydrogen, fluorine, chlorine, cyano, carboxyl, $C_1$-$C_4$-alkoxycarbonyl or $C_1$-$C_4$-alkylcarbonylamino, and $R^{10}$ represents formyl, cyano, carboxyl or hydroxymethyl, or $R^{10}$ together with $R^9$ represents —CO—O—CH$_2$CH$_2$—.

2. A naphthalene derivative according to claim 1, in which
$R^5$ represents methoxy,
$R^6$ represents hydrogen, and
$R^7$ represents methoxy.

3. A compound according to claim 1 wherein such compound is 2-(4,6-dimethoxypyrimidin-2-yl-pxy)-1-naphthaldehyde 4-cyano-phenylhydrazone.

4. A compound according to claim 1 wherein such compound is 2-(4,6-dimethoxypyrimidin-2-yl-oxy)-1-naphthaldehyde N-sec-butyl-phenylhydrazone.

5. A compound according to claim 1 wherein such compound is 2-(4,6-dimethoxypyrimidin-2-yl-oxy)-1-naphthaldehyde N-isopropyl-4-chlorophenylhydrazone.

6. A compound according to claim 1 wherein such compound is 2-(4,6-dimethoxypyrimidin-2-yl-oxy)-1-naphthaldehyde 4-tert-butyl-phenylhydrazone.

7. A herbicidal composition comprising a herbicidally effective amount of a compound according to claim 1 and a diluent.

8. A method of combating unwanted vegetation which comprises administering to such vegetation or to a locus from which it is desired to exclude such vegetation a herbicidally effective amount of a compound according to claim 1.

9. The method according to claim 6, wherein such compound is 2-(4,6-dimethoxypyrimidin 2-yl-oxy)-1-naphthaldehyde 4-cyano-phenylhydrazone,
2-(4,6-dimethoxypyrimidin 2-yl-oxy)-1-naphthaldehyde N-sec-butyl-phenylhydrazone,
2-(4,6-dimethoxypyrimidin 2-yl-oxy)-1-naphthaldehyde N-isopropyl-4-chlorophenylhydrazone or
2-(4,6-dimethoxypyrimidin .2-yl-oxy)-1-naphthaldehyde 4-tert-butyl-phenylhydrazone.

* * * * *

UNITED STATES PATENT AND TRADEMARK OFFICE
CERTIFICATE OF CORRECTION

PATENT NO. : 5,185,026
DATED : February 9, 1993
INVENTOR(S) : Drewes et al.

It is certified that error appears in the above-identified patent and that said Letters Patent is hereby corrected as shown below:

Col. 26, line 38  Delete "2-yl-pxy)" and substitute -- 2-yl-oxy)--

Signed and Sealed this

Twenty-sixth Day of July, 1994

Attest:

BRUCE LEHMAN

Attesting Officer  Commissioner of Patents and Trademarks